US005895753A

United States Patent [19]
Mierendorf et al.

[11] Patent Number: 5,895,753
[45] Date of Patent: Apr. 20, 1999

[54] METHOD FOR IN VITRO PROTEIN SYNTHESIS

[75] Inventors: Robert Mierendorf; Thomas R. Van Oosbree, both of Madison, Wis.

[73] Assignee: Novagen, Inc., Madison, Wis.

[21] Appl. No.: 08/938,481

[22] Filed: Sep. 30, 1997

Related U.S. Application Data

[63] Continuation of application No. 08/336,039, Nov. 8, 1994, abandoned.

[51] Int. Cl.$^6$ .................................................. C12N 5/00
[52] U.S. Cl. ........................ 435/68.1; 435/69.1; 435/70.1
[58] Field of Search .................................. 435/68.1, 70.1, 435/69.1

[56] References Cited

U.S. PATENT DOCUMENTS

| | | | |
|---|---|---|---|
| 5,324,637 | 6/1994 | Thompson et al. | 435/68.1 |
| 5,420,019 | 5/1995 | Theofan et al. | 435/69.1 |
| 5,665,563 | 9/1997 | Beckler | |

FOREIGN PATENT DOCUMENTS

PCT/SU90/ 00151  6/1990  WIPO.

OTHER PUBLICATIONS

Coen, et al., "Maize chloroplast DNA fragment encoding the large subunit of ribulosebisphosphat carboxylase," *Proc. Natl. Acad. Sci. USA*, 74:5487–5491 (1977).

Lewis, et al., "The Origin and Destiny of Adenovirus Proteins," *Cold Spring Harbor Symposium on Quantitative Biology*, vol. XXXIX pp. 581–590 ( ).

Perara & Lingappa, "A Former Amino Terminal Signal Sequence Engineered to an Internal Location Directs Translocation of Both Flanking Protein Domains," *The Journal of Cell Biology*, 101:2292–2301 (1985).

Stueber et al., "A novel in vitro transcription–translation system: accurate and efficient synthesis of single proteins from cloned DNA sequences," *IL Press Limited* 3143–3148 (1984).

Boehringer Mannheim, "Translation Kit, Reticulocyte, Type II," Cat. No. 1103 032 (1989).

Ball, et al., "Coupled Transcription and Translation in Mammalian and Avian Cell–Free Systems," *Virology* 84:479–495 (1978).

Bossart, et al., "Effect of UV Irradiation on the Expression of Vaccinia Virus Gene Products Synthesized in a Cell–Free System Coupling Transcription and Translation," *Journal of Virology* 26:673–680 (1978).

Content, et al., "Peptide Mapping Characterization of Viral Proteins Generated in a Cell–Free Coupled System for the Transcription and Translation of Influenza Virus mRNA," *Journal of Virology* 26:817–821 (1978).

Cooper, et al., "Transcription of Vaccinia Virus mRNA Coupled to Translation *In Vitro*," *Virology* 88:149–165 (1978).

Craig, et al., "Plasmid cDNA–directed protein synthesis in a coupled eukaryotic in vitro transcription–translation system," *Nucleic Acids Research* 20:4987–4995 (1992).

Dasso et al., "On the fidelity of mRNA translation in the nuclease–treated rabbit reticulocyte lysate system," *Nucleic Acids Research* 17:3129–3144 (1989).

Jackson, Richard J., "Potassium salts influence the fidelity of mRNA translation initiation rabbit reticulocyte lysates: unique features of encephalomyocarditis virus RNA translation," *Biochimica et Biophysico Acta* 1088:345–358 (1991).

Jagus,Rosemary, "Translation in Cell–Free Systems," *Methods in Enzymology* 152:267–276 (1987).

Kozak, Marilyn, "Context Effects and Inefficient Initiation at Non–AUG Codons in Eucaryotic Cell–Free Translation Systems," *Molecular and Cellular Biology* 9:5073–5080 (1989).

Krieg, et al., "Functional messenger RNAs are produced by SP6 in vitro transcription of cloned cDNAs," *Nucleic Acids Research* 12:7057–7070 (1984).

Kronenberg, et al., "The 3' noncoding region of β–globin mRNA is not essential for in vitro translation," *Nucleic Acids Research* 6:153–166 (1979).

Ledermann et al., "DNA–Directed Peptide Synthesis I. A Comparison of $T_2$ and *Escherichia coli* DNA–Directed Peptide Synthesis in Two Cell–Free Systems," *Biochim. Biophys. Acta* 149:253–258 (1967).

McCormick et al., "S•Tag™: A Multipurpose Fusion Peptide for Recombinant Proteins,".

Pelham, et al., "Characteristics of a Coupled Cell–Free Transription and Translation System Directed by Vaccinia Cores," *Eut. J. Biochem.* 82:199–209 (1978).

Perara, et al., "A Former Amino Terminal Signal Sequence Engineered to an Internal Location Directs Translocation of Both Flanking Protein Domains," *The Journal of Cell Biology* 101:2292–2301 (1985).

Roberts, et al., "Simian Virus 40 DNA Directs Synthesis of Authentic Viral Polypeptides in a Linked Transcription–Translation Cell–Free System," *Proc. Nat. Acad. Sci. USA* 72:1922–1926 (1975).

Rozenblatt, et al., "Direct biochemical mapping of eukaryotic viral DNA by means of a linked transcription–translation cell–free system," *Proc. Natl. Acad. Sci. USA* 73:2747–2751 (1976).

Sambrook, et al., "Translation of Reticulocyte Lysates," *Detection and Analysis of Proteins Expressed from Cloned Genes*.

Spirin, et al., "A Continuous Cell–Free Translation System of Producing Polypeptides in High Yield," *Science* 242:1162–1164 (1988).

Spirin, ALexander S., "Cell–Free Protein Synthesis Bioreactor," *Institute of Protein Research* 31–43 (1992).

*Primary Examiner*—Leon B. Lankford, Jr.
*Attorney, Agent, or Firm*—Quarles & Brady

[57] ABSTRACT

A method for performing coupled in vitro transcription and translation reactions is disclosed In the transcription reaction, the quantity of mRNA produced is limited to a level of less than about 2.5 micrograms in a 10 microliter volume prior to the translation elements being added. Limiting the level of mRNA produced prevents saturation of the translational processes and thus aids in the efficiency and fidelity of the translation process.

8 Claims, 2 Drawing Sheets

5,895,753

1

METHOD FOR IN VITRO PROTEIN SYNTHESIS

This is a continuation of application Ser. No. 08/336,039 filed Nov. 8, 1994 now abandoned.

FIELD OF THE INVENTION

The present invention relates to a method for the in vitro production of protein in which input DNA is transcribed and translated in a two-step reaction performed in a single vessel at a constant temperature.

BACKGROUND OF THE INVENTION

The techniques of modern molecular biology have made possible the manipulation of DNA as well as the other cellular components expressed from the genes contained in the DNA of an organism. In living cells, DNA is transcribed to make mRNA which is then used as a template, in a process called translation, to make a protein whose sequence is determined by the DNA. In developing the modern tools of molecular biology, research has been directed toward ways to perform various steps of the transcription or translation processes in vitro under controlled conditions and with defined inputs. These procedures mimic, in essence, similar processes that occur in a much more heterogeneous mixture in living cells.

Even before the advent of modern recombinant technology, cell extracts were developed which allowed the synthesis of protein in vitro from purified mRNA transcripts. Since that time, several systems have become widely available and are used for the study of protein synthesis and RNA structure and function. To synthesize a protein under investigation, a translation extract must be "programmed" with an mRNA corresponding to the gene or protein under investigation. The mRNA is most often added exogenously in purified form. Historically, such mRNA templates were purified from natural sources or, using more recently developed technologies, prepared synthetically from cloned DNA using bacteriophage RNA polymerases in an in vitro reaction. The preparation of such mRNAs, even by in vitro synthesis, remains a rather tedious process, and this difficulty has limited the practical utility of in vitro translation for a number of applications.

There has consequently been a significant effort in a number of laboratories to develop either coupled or complementary transcription and translation systems which carry out the synthesis of both RNA and protein in the same reaction, beginning with input DNA. These extracts must contain all the components necessary both for transcription (to produce mRNA) and for translation in a single system. In such a system, the input is DNA, which is normally much easier to obtain than RNA and much more readily manipulable. The first such coupled system was based on a bacterial extract. Lederman and Zubay, Biochim. Biophys. Acta, 149:253 (1967). Since prokaryotes normally carry out a coupled reaction within their cytoplasm in any event, this system closely reflected the in vivo process and remains widely used for the study of prokaryotic genes. However, this system is generally not useful for eukaryotic genes, due to its inefficiency and relatively high nuclease content.

Eukaryotic extracts have also been defined that use exogenously added E. coli RNA polymerase or wheat germ RNA polymerase to transcribe exogenous DNA. These systems have had limited success for the general study of eukaryotic genes, due to their low efficiency, and to the fact that they were developed and used prior to the widespread success of

2 cDNA cloning techniques. Other coupled systems have been developed for the study of viral protein synthesis, but are not generally useful for non-viral templates.

In the mid-1980s, the development of highly efficient in vitro transcription systems, particularly ones using phage polymerases such as T7, SP6, and T3, allowed systems to be defined to more efficiently translate cloned mRNA sequences in vitro using translation extracts from wheat germ and rabbit reticulocytes. Perara and Lingappa showed that SP6 RNA polymerase transcription reactions could be added directly to reticulocyte lysate for the production of protein, an insight which illuminated the need to purify the mRNA prior to translation. J. Cell Biol. 101:2292–2301 (1985). Later other workers showed that the transcription and translation could be coupled in reticulocyte lysate by including a phage polymerase and appropriate transcriptional co-factors in the reaction. Spirin et al., Science 242:1162–1164 (1988); Craig et al., Nucleic Acids Res. 20:4987–4995 (1992). More recently, U.S. Pat. No. 5,324,637 describes a coupled transcription and translational system, using reticulocyte lysate and including a phage polymerase, in which the coupling of the two reactions is facilitated by specific conditions, notably the concentration of magnesium ions, which permit both transcription and translation to occur in the same reaction.

Although the coupled approach for transcription and translation systems is useful for many proteins, translation efficiencies can vary widely depending on the type of DNA template which is used (e.g., supercoiled plasmid DNA or linear DNA). In addition, the amount of mRNA synthesized in a coupled reaction is difficult to control under most coupled conditions, such as those described in the aforesaid U.S. Pat. No. 5,324,637. Since the efficiency and fidelity of translation are dependent upon the amount of mRNA added to the reaction, a possible explanation for the undesirable variability of results in a coupled system, in which the reactions occur simultaneously, is that transcription is not consistent between various templates under coupled conditions. Moreover, coupled systems exhibit a marked dependence on the magnesium concentration for the translation efficiency of various templates.

SUMMARY OF THE INVENTION

The present invention is summarized in that a two-step method for transcription and then translation occurs in a single vessel and at a single temperature. One reaction mixture is added to the vessel to create mRNA from a DNA template, with the reaction conditions controlled to limit the concentration of mRNA in the reaction mix. Then, a second set of constituents is added to the same reaction, the second set of constituents effectuating the translation reaction. The result is a dual-stage transcription/translation protocol in which protein is produced in an efficient manner, and at a constant temperature, in a single vessel.

It is an object of the present invention to describe a two-stage transcription/translation methodology which results in a consistent production of protein regardless of the topography of the input DNA.

It is another object of the present invention to provide a two-stage transcription and translation system which is convenient and efficient to operate and can occur at modest temperatures and in short time frames.

Other objects, advantages, and features of the present invention will become apparent from the following specification.

DETAILED DESCRIPTION OF THE INVENTION

Figure 1:
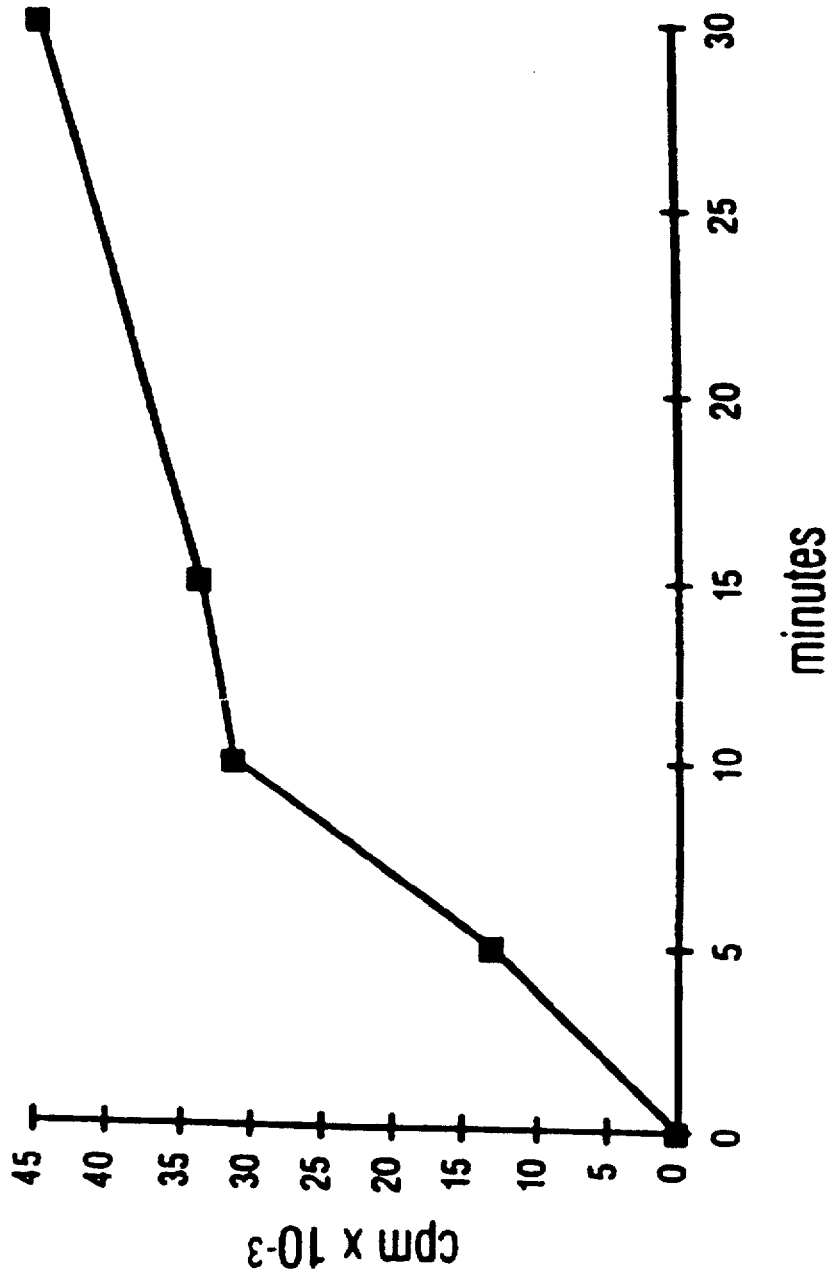
FIG. 1 is a graphical representation of transcription over time.

The present invention is directed toward a method of performing transcription and then translation using a two-step approach of complementary reactions. The reaction mixture for the transcription reaction is carefully constructed so as, contrary to all prior teachings in the art, to limit the synthesis of mRNA and consequently limit the amount of mRNA to be provided to the translation reaction. Previously, conditions for transcription were usually optimized for maximum production of mRNA. However, it has been discovered that the faithful and efficient production of protein in the translation reaction is facilitated if the initial amount of input mRNA is limited, as described below.

The preferred method in accordance with the present invention contemplates that two separate reactions, i.e. transcription and then translation, will be carried out in a common vessel at a common temperature. A transcription reaction mixture is added to the vessel and provided with template DNA which is to be transcribed. The transcription reaction is then incubated so that transcription is allowed to occur. Then, a translation reaction mixture is added to the same vessel, which has the effect of diluting the transcription reaction mixture by the volume of the translation reaction mixture that is added. The temperature is unchanged and the reaction continues in the same vessel. By limiting the amount of mRNA synthesized to a level between 0.5 and 2.5 micrograms in a 10 microliter reaction (i.e. about 0.05-0.25 µg mRNA per µl of reaction volume), high translation efficiency is maintained without a loss of fidelity in the size or sequence of the protein ultimately produced. Below 0.5 µg, the reaction is inefficient in use of reagents while above 2.5 µg, the amount of mRNA produced can over saturate the translational system for some RNAs. The preferred value is 1 microgram of mRNA in a 10 microliter volume, or 0.1 µg/µl. A level of 0.1 µg/µl in the transcription mixture corresponds to 0.02 µg/µl or 20 µg/ml in the subsequent translation mixture.

There are several ways in which the amount of mRNA synthesized during the transcription reaction can be limited. This can be accomplished in any of a variety of ways that maintain the quality and integrity of the mRNA synthesized, as intact chains, and maintain the compatibility of the reaction with the direct addition of a translation reaction mixture that would allow efficient protein synthesis. In the method described below, the limiting factors include the limited amount of nucleotide triphosphates (NTP's) and magnesium ions available to the reaction, and the performance of the reaction at a modest temperature for a relatively brief time period. In practice, these conditions can be modified, i.e., by increasing one component and decreasing another, while still holding the amount of mRNA synthesized to the required level of 0.5 to 2.5 µg per 10 µl reaction.

In its preferred embodiment, a preferred and convenient transcription reaction mixture and a translation reaction mixture have been developed. These constituents have been developed for a reaction in which the transcription reaction will occur in 10 microliters incubated at 30° C. for 15 minutes. Following that, one would add 40 microliters of the translation reaction mixture and continue to incubate at 30° C. for 60 to 90 minutes for translation to occur. Each of the transcription and translation reaction mixtures can be separately pre-mixed, so that the only reagents which need to be added to the two reaction mixtures are the input DNA template, water, and a choice of either unlabeled methionine or $^{35}$S-methionine, if a radioactive tracer is desired. Other amino acids containing radioactive isotopes or other detectable chemical groups (e.g., biotin) may be substituted by modifying the amino acid supplements accordingly, as is common in the art.

Transcription Reaction Mixture 1. 76.8 mM Hepes-KOH buffer, pH 7.6
2. 4.8 mM magnesium acetate
3. 9.6 mM sodium chloride
4. 1.92 mM spermidine
5. 96 µg/ml acetylated bovine serum albumin
6. 4.8 mM dithiothreitol
7. 0.192 mM each of ATP, CTP, GTP, and UTP
8. 0.8 units/µl placental ribonuclease inhibitor
9. 6.4 units/µl T7 RNA polymerase
10a. 0.5 µg plasmid DNA template with T7 promoter
10b. 2 µl PCR DNA with T7 promoter

Translation Reaction Mixture 1. 50% rabbit reticulocyte lysate, nuclease treated
2. 75 mM potassium acetate
3. 0.45 mM each of ATP, CTP, GTP, and UTP
4. 2.5 mM dithiothreitol
5. 25 mM Hepes-KOH buffer, pH 7.6
6. 10 mM creatine phosphate
7. 31.25 µM 19 amino acids minus methionine
8a. 31.25 µM methionine for a nonradioactive reaction
8b. 1 µCi/µl $^{35}$S-methionine for a radioactive reaction It can be readily understood that by combining the above two components, a total reaction mixture during the translation part of the process will have a volume of 50 microliters. Calculating out the total concentration of the various constituents of the two mixtures in the total reaction mixture gives the following values.

Final Reaction Mixture 1. 40% rabbit reticulocyte lysate, nuclease treated
2. 60 mM potassium acetate
3. 0.3984 mM each of ATP, CTP, GTP, and UTP
4. 2.96 mM dithiothreitol
5. 35.4 mM Hepes-KOH buffer, pH 7.6
6. 8 mM creatine phosphate
7. 25 µM 19 amino acids minus methionine
8a. 25 µM methionine for a nonradioactive reaction
8b. 0.8 µCi/µl $^{35}$S-methionine for a radioactive reaction
9. 0.96 mM magnesium acetate
10. 1.92 mM sodium chloride
11. 0.384 mM spermidine
12. 19.2 µg/ml acetylated bovine serum albumin
13. 0.16 units/µl ribonuclease inhibitor
14. 1.28 units/µl T7 RNA polymerase
15a. 0.5 µg plasmid DNA template with T7 promoter
15b. 2 µl PCR DNA with T7 promoter In each of the tables above, where the reaction mixtures includes alternatives, they have been given the same numeral but with an alternate designation, e.g. 10a. and 10b. or 8a. and 8b.

Of the constituents of the two above reaction mixtures, in the transcription reaction mixture, the salts are simply to maintain appropriate ionic conditions to promote transcription and translation. The spermidine is, as is well known to the art, a poly cation which binds to DNA and maintains it in an accessible condition. The serum albumin is a neutral protein carrier to prevent surface interactions of the RNA polymerase and ribonuclease inhibitor. Dithiothreitol is a protein protectant to help maintain the efficacy of enzymes in in vitro solutions. The ribonuclease inhibitor is intended to prevent degradation of the mRNA products which are, after ell, the objective of the reaction. The T7 RNA polymerase catalyzes the transcription of mRNA from a DNA template. Clearly, for each of these components, other suitable substitutions can be found to have similar effects. For example, a wide variety of promoters are available and are known to be efficacious for in vitro RNA synthesis, and several of such promoters are phage promoters which have particular specificity and utility for in vitro usage. Those of ordinary skill in the art will readily understand that substitutions to these particular constituents can be made without effecting the overall efficacy of the mixture or the method of its use.

Similarly, in the translation reaction mixture, the rabbit reticulocyte lysate provides, of course, the protein translation assembly necessary to make the proteins. Other cell lysate systems, such as wheat germ lysate can be used as well, as can an assembly of intact ribosomes and translation factors. What is required is simply in vitro competent translation components. The salts and NTPs present in the translation mixture are for proper functioning of translation components. The amino acids are the constituents from which the protein is made and, obviously, one or more amino acids can be tagged radioactively, or tagged by other methods, so as to be detectable in the final expressed protein product. Again, many substitutions for these individual constituents are possible given the ordinary level of skill in the art.

Performing the transcription step in a separate reaction has two major advantages. First it permits control over the amount of mRNA synthesized by adjusting the various reaction components for the transcription reaction without great concern about the effect on the translation reaction. Secondly, it allows for optimal translation in the presence of a single magnesium concentration. A single magnesium concentration (approximately 1 mM) is useful for translation of many types of RNA in a reticulocyte lysate, including both uncapped mRNA as well as uncapped in vitro transcription products from non-EMC and EMC-containing vectors. EMC refers to the 5' non-coding region of the encephalomyocarditis virus, which functions as an internal entry point for initiation of translation by eukaryotic ribosomes, and thus dramatically increases the in vitro translation efficiency of synthetic RNA by reticulocyte lysates. In addition, magnesium concentrations in the range of about 1 mM appear to allow more accurate initiation of translation for standard (non-EMC) RNA transcripts. The reaction mixtures above were optimized to permit efficient protein synthesis simply by adding a translation mix directly to the reaction, and assuming that both reactions would be incubated at the same temperature, i.e. 30° C.

The theory behind the approach of the present invention is that translation efficiency and fidelity vary with the concentration of mRNA in a reaction. Protein synthesis increases in a linear fashion with increasing concentration of mRNA until a maximum or saturation is reached. Higher concentrations of mRNA lead to a decrease in full-length protein products and total amount of protein produced. Different mRNAs saturate the translation process at different concentrations. Globin mRNA, which is the natural template for reticulocyte lysate, saturates at a concentration of 20 µg/ml. Most mRNAs appear to saturate at concentrations between 5 and 80 µg/ml. In spite of this, mRNA concentrations of 5 to 20 µg/ml are often recommended for translation reactions. Our results are consistent with these levels, since we find that transcription conditions limited to produce about 1 µg of RNA in a 10 µl transcription reaction are optimal for translation in 50 µl, which corresponds to an RNA concentration of 20 µg/ml in the translation mixture. Thus by limiting conditions to produce between 0.05 and 0.25 µg/µl in the transcription reaction, the physiologically optimal range of 10–50 µg/ml is achieved. Our results suggest that at high concentrations (>100 µg/ml), the mRNA titrates one or more of the factors responsible for accurate translation initiation and termination, and that an over abundance of mRNA causes the appearance of shortened products that represent aberrant initiation at internal sites in the mRNA as well as premature termination of elongated polypeptide chains.

It is to be well understood by those of ordinary skill in the art that the idealized reaction mixtures presented above contain a variety of components, such as salts and buffers, for which ready substitutions are possible. It is also apparent that these reaction mixtures are calculated for certain total reaction volumes, and that the concentrations and amounts would be varied for a different volume of reactions.

Examples

Transcription Time Course A series of experiments of the transcription reaction, with translation begun at various incubation times, were undertaken with the transcription reaction mixture and the translation reaction mixture as described above. The DNA template used for this reaction was the STP control template (*E. coli* β-galactosidase in a pCITE® vector) and the RNA polymerase used was the T7 RNA polymerase. All reactions were performed at 30° C. and in the presence of $^3$H-CTP. At time intervals from initiation of the transcription reaction, two microliter aliquots were removed from the reaction mixture for measurement of the total RNA synthesis by TCA precipitation. Duplicate 10 microliter aliquots were added to 40 microliter translation mix containing $^{35}$S-methionine and incubated at 30° C. for an additional 90 minutes. The amount of protein synthesized was quantitatively analyzed using the S-Tag Rapid Assay Kit (Novagen) which allows for the non-radioactive assay of quantitative amounts of protein translated in vitro. The S-Tag sequence is a 15 amino acid leader peptide which, when present in a translated protein, can be detected using the S-Tag Rapid Assay Kit. The amount of protein production was also verified by radiographic analysis of $^{35}$S-labeled β-galactosidase following SDS gel electrophoresis.

Figure 2:
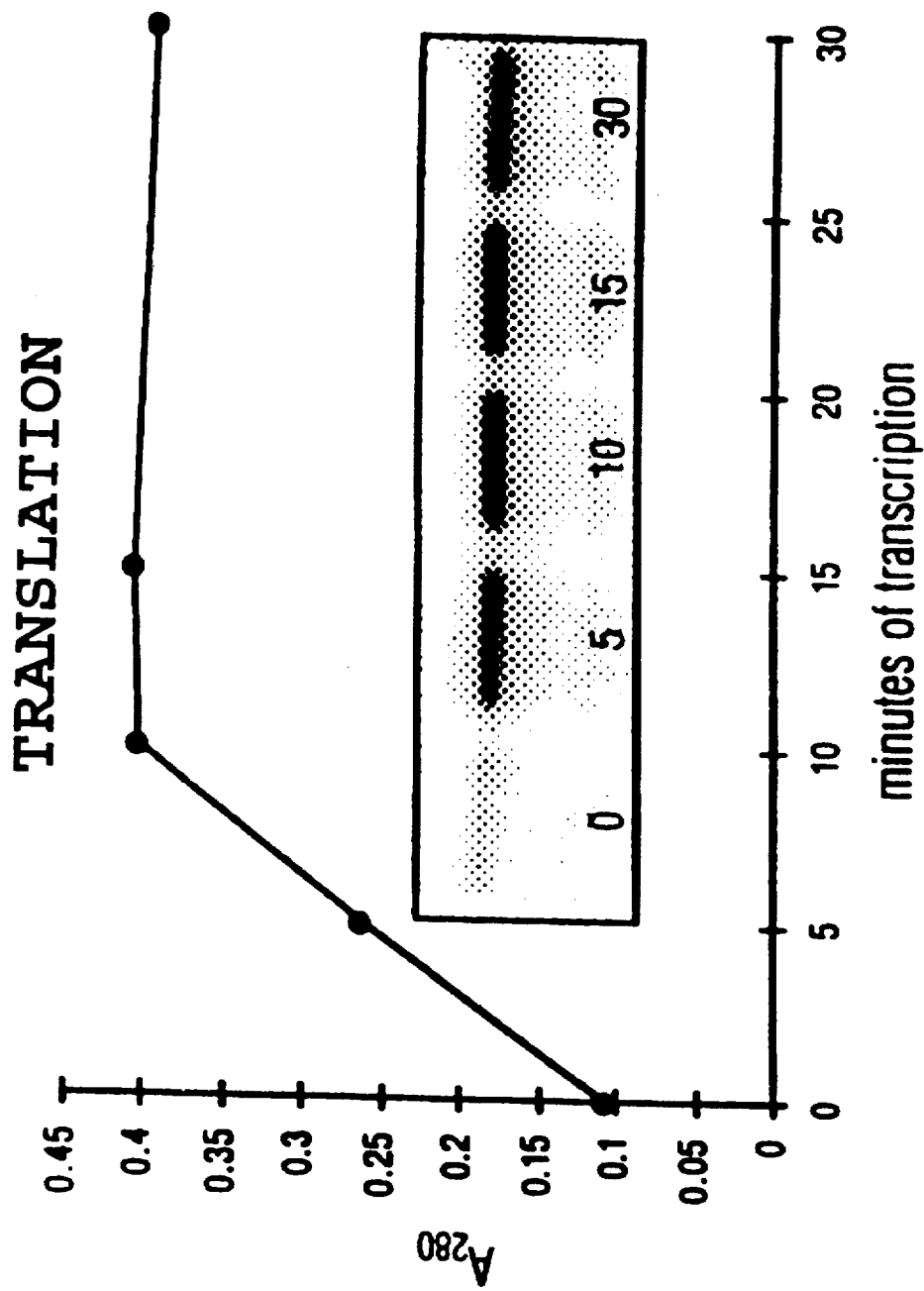
FIG. 2 is a graphical representation of the translation that occurs from transcription reactions carried out over time.

The results of these experiments are illustrated in FIGS. 1 and 2. FIG. 1 illustrates the time course for transcription. The data demonstrate that transcription is 80% complete within 10 minutes at 30° C. The translation data, shown in FIG. 2, provide a similar conclusion in that almost all of the translatable mRNA was synthesized within the first 15 minutes of transcription.

Effect of Magnesium Concentration The procedure of the present invention was performed under standard conditions, with the transcription reaction mixture and the translation reaction mixture described above using three template DNAs. One template DNA is the vector pCITE, which includes a phage promoter and a cap independent translation enhancer sequence driving a coding region which, in this instance, was the enzyme β-galactosidase. A second template was the vector pET CRE which is a pET vector (Novagen) containing the gene for bacteriophage P1 cre recombinase. The third template used was a pGEM (Promega) vector into which had been inserted a gene coding sequence for the firefly luciferase protein.

All three plasmids were introduced into 10 microliters of the transcription reaction mixture described above. Following incubation for 15 minutes at 30° C., 40 microliters of the translation mixture was added to the vessel. The translation mix contained $^{35}$S-methionine and varying amounts of magnesium acetate, either 1, 1.5, or 2.5 mM. All three templates produced optimal translation in the presence of approximately 1 mM magnesium acetate under standard conditions, as determined by fluorographic analysis of SDS-PAGE gels. The amount of protein synthesis markedly declined at a concentration of 2.5 mM magnesium acetate. Additional experiments performed under similar conditions demonstrated that magnesium concentrations below 0.8 mM also result in lower translation efficiency for all three templates. These data indicate that the most efficient translation of all template types occurs at a magnesium concentration in the range of 1 mM in the final mix of transcription and translation mixtures.

To investigate the efficacy of this protocol with a wide variety of DNA templates, several plasmid and PCR template DNAs were created and then used as a template in the dual stage reaction described herein. Two of the templates were prokaryotic proteins, including *E. coli* β-galactosidase and P1 cre recombinase. Several eukaryotic protein sequences were used as well, including firefly luciferase, mouse tropomyosin, a recombinant antibody construct, and encephalomyocarditis VP0 protein. Again the production of protein was visualized and quantified by SDS-PAGE electrophoresis and fluorography. One class of templates which proved to be particularly efficiently translated were the templates carrying the CITE sequence of the EMC enhancer. However, all templates were transcribed and translated with efficiency. The PCR amplification products, containing upstream T7 promoter with or without a CITE sequence, also served as efficient templates for protein production. The same PCR templates produce little or no protein when added to another commercially available reticulocyte lysate based transcription/translation system. This demonstrated that the transcription and translation method of the present invention is applicable to a wide variety of DNAs and PCR transcription products without particular specificity to any given template.

We claim:

1. A method of performing in vitro transcription and translation comprising the steps of
    (a) placing in a vessel a template DNA together with a transcription reaction mixture which comprises selected concentrations of ribonucleotide triphosphates together with an RNA polymerase, DNA protectants and an ionic concentration favorable for transcription;
    (b) incubating the vessel under incubation conditions favorable to transcription of the template DNA, the selection of the concentrations of ribonucleotide triphosphates in the transcription reaction mixture being such that the concentration of transcribed mRNA in the vessel after transcription is completed in between about 0.05 and about 0.25 μg of transcribed mRNA per μl of reaction mixture, the incubating continuing past the point at which transcription ceases;
    (c) adding directly to the unpurified transcription reaction mixture a translation reaction mixture including a eukaryotic cell lysate and amino acids sufficient for the translation of protein from the transcribed mRNA, the concentration of mRNA in the combined mixture being between about 0.01 and 0.05 μg of mRNA per μl of reaction mixture; and
    (d) incubating the mixture created in step (c) under conditions favorable to translation.

2. A method as claimed in claim 1 wherein the steps (a), (b), (c) and (d) are all conducted in the same vessel.

3. A method as claimed in claim 1 wherein both steps (b) and (c) are conducted at the same temperature.

4. A method as claimed in claim 1 wherein the combination of selected conditions includes performing step (b) at 30° C. for about fifteen minutes.

5. A method as claimed in claim 1 wherein the salts in the transcription reaction mixture include a magnesium salt, and wherein the concentration of the magnesium salt is selected so that after step (c) the concentration of magnesium is no more than about 1 mM.

6. A method of performing in vitro transcription and translation comprising the steps of
    (a) placing in a vessel a template DNA together with a transcription reaction mixture which includes about 0.2 mM of all four ribonucleotide triphosphates, a RNA polymerase, and ionic concentrations favorable for transcription;
    (b) incubating the vessel at about 30° C. for about fifteen minutes such that transcription is completed and the concentration of mRNA in the vessel is between about 0.05 and about 0.25 μg of transcribed mRNA per μl of reaction mixture;
    (c) adding to directly to the vessel containing the reaction products of the transcription reaction a translation reaction mixture including a eukaryotic cell lysate and all twenty amino acids which occur in eukaryotic proteins, the relative volumes of the combined transcription and translation mixtures being such that the concentration of mRNA in the combined reaction mixtures is less than about 0.05 μg of mRNA per μl; and
    (d) incubating the mixture created in step (c) in the same vessel at about 30° C. so that translation can proceed.

7. A method as claimed in claim 6 wherein the salts in the transcription reaction mixture include a magnesium salt, and wherein the concentration of the magnesium salt is selected so that after step (c) the concentration of magnesium is no more than about 1 mM.

8. A method as claimed in claim 1 wherein the concentration of mRNA in the vessel in step (b) does not exceed about 0.1 μg/μl.

* * * * *